United States Patent
Haji Reza et al.

(10) Patent No.: US 11,950,882 B2
(45) Date of Patent: *Apr. 9, 2024

(54) SINGLE SOURCE PHOTOACOUSTIC REMOTE SENSING (SS-PARS)

(71) Applicant: ILLUMISONICS INC., Waterloo (CA)

(72) Inventors: Parsin Haji Reza, Waterloo (CA); Kevan Bell, Waterloo (CA)

(73) Assignee: ILLUMISONICS INC., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,791

(22) Filed: Dec. 21, 2022

(65) Prior Publication Data

US 2023/0225618 A1 Jul. 20, 2023

Related U.S. Application Data

(63) Continuation of application No. 16/647,076, filed as application No. PCT/IB2020/051804 on Mar. 3, 2020, now Pat. No. 11,564,578.
(Continued)

(51) Int. Cl.
*A61B 5/00* (2006.01)
*A61B 1/00* (2006.01)
(Continued)

(52) U.S. Cl.
CPC ........ *A61B 5/0095* (2013.01); *A61B 1/00004* (2013.01); *A61B 1/00172* (2013.01);
(Continued)

(58) Field of Classification Search
CPC .............. A61B 5/0095; A61B 1/00004; A61B 1/00172; A61B 1/0615; A61B 5/0035;
(Continued)

(56) References Cited

U.S. PATENT DOCUMENTS

| | | |
|---|---|---|
| 5,070,733 A | 12/1991 | Nagata et al. |
| 5,479,259 A | 12/1995 | Nakata et al. |

(Continued)

FOREIGN PATENT DOCUMENTS

| | | |
|---|---|---|
| CN | 101526483 A | 9/2009 |
| CN | 103048271 A | 4/2013 |

(Continued)

OTHER PUBLICATIONS

Beard, Paul. "Biomedical Photoacoustic Imaging." Interface Focus 1.4 (2011): 602-631. PMC. Web. Dec. 12, 2017.
(Continued)

*Primary Examiner* — Md M Rahman
(74) *Attorney, Agent, or Firm* — Bookoff McAndrews, PLLC

(57) ABSTRACT

A photoacoustic remote sensing system for imaging a subsurface structure in a sample, comprising exactly one laser source configured to generate a pulsed or intensity-modulated excitation beam configured to generate ultrasonic pressure signals in the sample at an excitation location, and an interrogation beam incident on the sample at the excitation location, a portion of the interrogation beam returning from the sample that is indicative of the generated ultrasonic pressure signals, an optical system configured to focus the excitation beam and the interrogation beam below a surface of the sample, a detector configured to detect the returning portion of the interrogation beam, and a processor configured to calculate an image of the sample based on a detected intensity modulation of the returning portion of the interrogation beam from below the surface of the sample.

20 Claims, 8 Drawing Sheets

Related U.S. Application Data

(60) Provisional application No. 62/818,967, filed on Mar. 15, 2019.

(51) Int. Cl.
   *A61B 1/06* (2006.01)
   *A61B 5/02* (2006.01)
   *A61B 5/145* (2006.01)
   *G01N 21/17* (2006.01)
   *G01N 21/64* (2006.01)

(52) U.S. Cl.
   CPC .......... *A61B 1/0615* (2013.01); *A61B 5/0035* (2013.01); *A61B 5/14532* (2013.01); *A61B 5/14542* (2013.01); *G01N 21/1702* (2013.01); *G01N 21/64* (2013.01); *A61B 1/00117* (2013.01); *A61B 5/02042* (2013.01); *G01N 2021/1706* (2013.01); *G01N 2201/0683* (2013.01); *G01N 2201/08* (2013.01)

(58) Field of Classification Search
   CPC ............ A61B 5/14532; A61B 5/14542; A61B 1/00117; A61B 5/02042; G01N 21/1702; G01N 21/64; G01N 2021/1706; G01N 2201/0683; G01N 2201/08
   USPC ......................................................... 356/502
   See application file for complete search history.

(56) References Cited

U.S. PATENT DOCUMENTS

| | | | |
|---|---|---|---|
| 5,615,675 | A | 4/1997 | O'Donnell et al. |
| 5,991,479 | A | 11/1999 | Kleinerman |
| 6,016,202 | A | 1/2000 | Fuchs et al. |
| 6,078,397 | A | 6/2000 | Monchalin et al. |
| 6,256,100 | B1 | 7/2001 | Banet et al. |
| 6,973,830 | B2 | 12/2005 | Pepper et al. |
| 6,992,829 | B1 | 1/2006 | Jennings et al. |
| 7,068,842 | B2 | 6/2006 | Liang et al. |
| 8,004,689 | B2 | 8/2011 | Monchalin et al. |
| 8,180,134 | B2 | 5/2012 | Wang |
| 8,454,512 | B2 | 6/2013 | Wang et al. |
| 8,692,155 | B2 | 4/2014 | Bischoff et al. |
| 9,153,931 | B2 | 10/2015 | Ichihara et al. |
| 9,999,354 | B2 | 6/2018 | Rousseau et al. |
| 2006/0184042 | A1 | 8/2006 | Wang et al. |
| 2006/0262316 | A1 | 11/2006 | Baney |
| 2008/0123083 | A1 | 5/2008 | Wang et al. |
| 2008/0194929 | A1 | 8/2008 | Pesach et al. |
| 2009/0170149 | A1 | 7/2009 | Viator et al. |
| 2010/0157308 | A1 | 6/2010 | Xie |
| 2010/0268042 | A1 | 10/2010 | Wang et al. |
| 2012/0200845 | A1 | 8/2012 | Rousseau et al. |
| 2012/0320368 | A1 | 12/2012 | Jiao et al. |
| 2014/0009808 | A1 | 1/2014 | Wang et al. |
| 2014/0060189 | A1 | 3/2014 | Sausa et al. |
| 2014/0118749 | A1 | 5/2014 | Nakajima et al. |
| 2014/0185055 | A1 | 7/2014 | Wang |
| 2014/0247456 | A1 | 9/2014 | Horstmann et al. |
| 2015/0077819 | A1 | 3/2015 | Schnell et al. |
| 2015/0148655 | A1 | 5/2015 | Haupt et al. |
| 2015/0150465 | A1 | 6/2015 | Irisawa et al. |
| 2015/0153269 | A1 | 6/2015 | Nakatsuka |
| 2015/0164337 | A1 | 6/2015 | Kim et al. |
| 2015/0185187 | A1 | 7/2015 | Wang et al. |
| 2015/0221081 | A1 | 8/2015 | Chang et al. |
| 2015/0265156 | A1 | 9/2015 | Tanaka |
| 2016/0113507 | A1 | 4/2016 | Reza et al. |
| 2017/0205377 | A1 | 7/2017 | Garnett et al. |
| 2017/0215738 | A1 | 8/2017 | Haji Reza et al. |
| 2018/0095026 | A1 | 4/2018 | Prasad |

FOREIGN PATENT DOCUMENTS

| | | |
|---|---|---|
| CN | 109363639 A | 2/2019 |
| DE | 10 2010 012 809 A1 | 9/2011 |
| JP | 2001228123 A | 8/2001 |
| JP | 2003215110 A | 7/2003 |
| JP | 2010185772 A | 8/2010 |
| WO | 2009055705 A2 | 4/2009 |
| WO | 2009055705 A3 | 6/2009 |
| WO | 2013023210 A1 | 2/2013 |
| WO | 2013166044 A1 | 11/2013 |
| WO | 2014027316 A2 | 2/2014 |
| WO | 2014036405 A2 | 3/2014 |
| WO | 2014062529 A1 | 4/2014 |
| WO | 2014160116 A1 | 10/2014 |
| WO | 2014168930 A1 | 10/2014 |

OTHER PUBLICATIONS

International Search Report and Written Opinion dated Dec. 19, 2018 in International Application No. PCT/IB2018/057585 (25 pages).

Kevan L. Bell et al., "Coherence-gated photoacoustic remote sensing microscopy", Optics Express, vol. 26, No. 18, Sep. 3, 2018, 16 pp.

Zhihua Ding et al., "Real-time phase-resolved optical coherence tomography and optical Doppler tomography", Optics Express, vol. 10, No. 5, Mar. 11, 2002, 10 pages.

Cedric Blatter et al., "Intrasweep phase-sensitive optical coherence tomography for noncontact optical photoacoustic imaging", Optics Letters, vol. 37, No. 21, Nov. 1, 2012, 4 pp.

Adhikari et al., "Photothermal Microscopy: Imaging the Optical Absorption of Single Nanoparticles and Single Molecules," ACS Nano 2020, 14 (12), 16414-16445 (32 pages).

Tavakolian et al., "Perspective: Principles and specifications of photothermal imaging methodologies and their applications to non-invasive biomedical and non-destructive materials imaging," J. Appl. Phys. 124, 160903 (2018) (13 pages).

Office Action dated Sep. 12, 2023 in Japanese Patent Application No. 2021-555290 (3 pages).

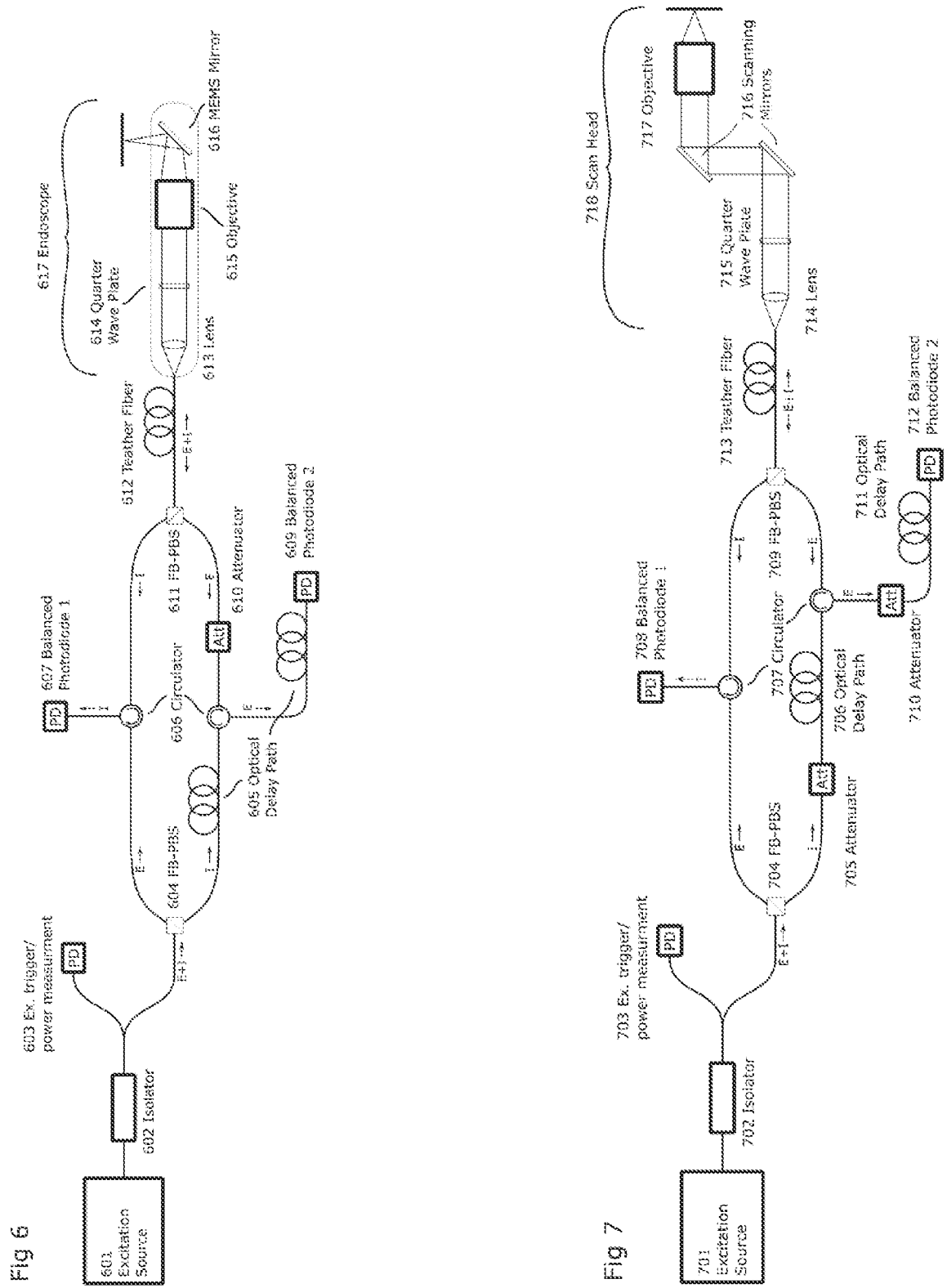

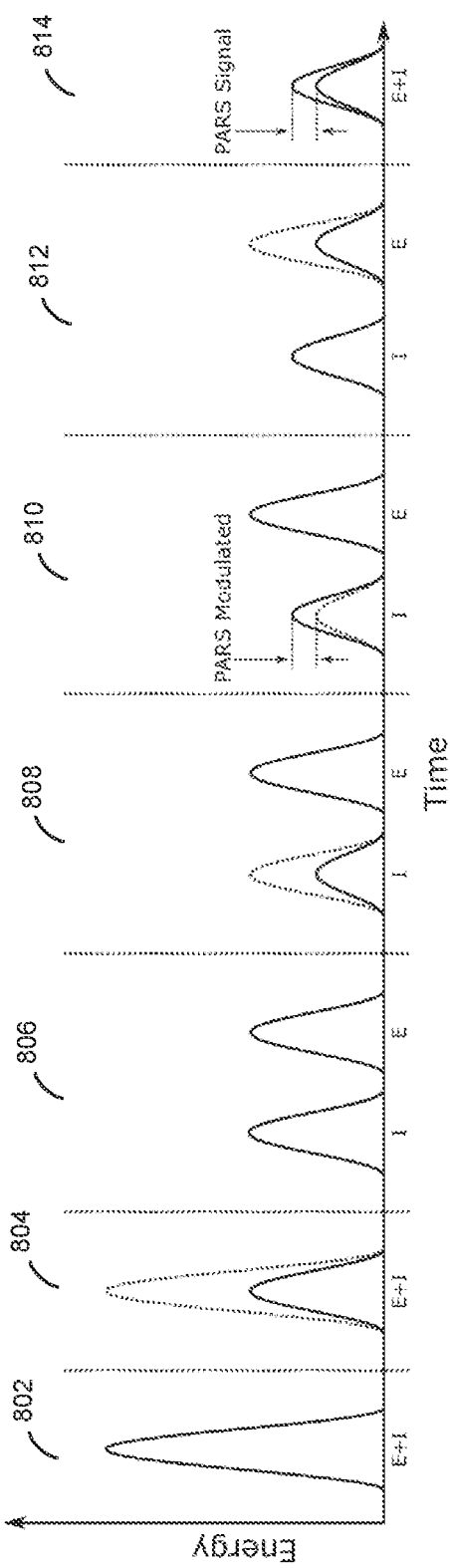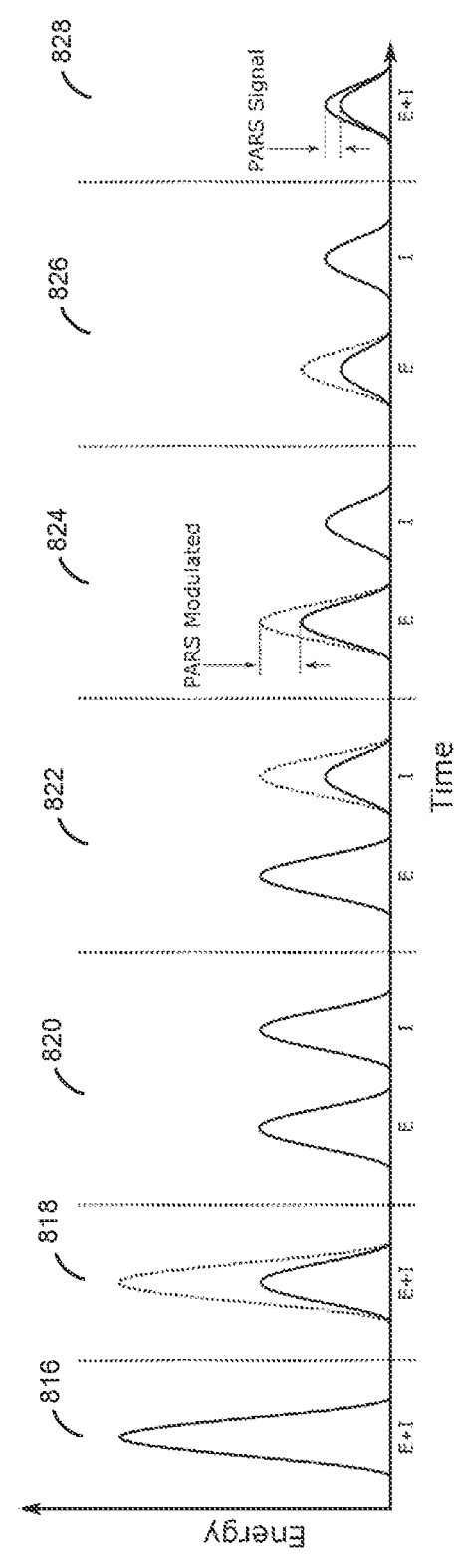

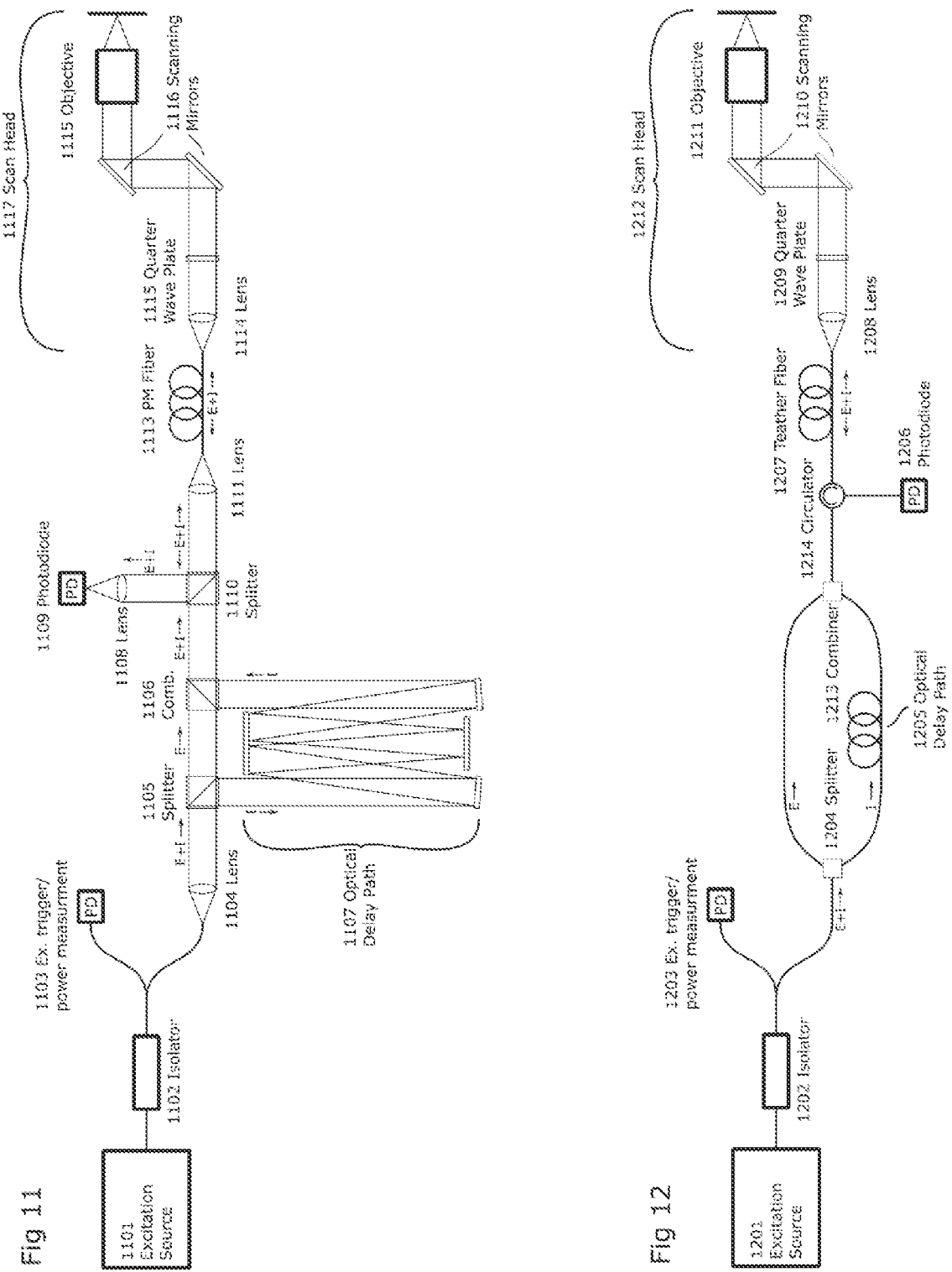

SINGLE SOURCE PHOTOACOUSTIC REMOTE SENSING (SS-PARS)

CROSS-REFERENCE TO RELATED APPLICATION(S)

This patent application is a continuation of U.S. patent application Ser. No. 16/647,076, filed Mar.13, 2020, which is a U.S. national stage filing under 35 U.S.C. § 371 of International Application No. PCT/IB2020/051804, filed Mar. 3, 2020, which claims benefit of priority under 35 U.S.C. § 119 to U.S. Provisional Patent Application No. 62/818,967, filed Mar. 15, 2019, the entirety of which is incorporated herein by reference.

FIELD

This relates to the field of optical imaging and, in particular, to a laser-based method and system for non-contact imaging of biological tissue in vivo, ex vivo, or in vitro.

BACKGROUND

The entireties of the U.S. Patents and Patent Publications set forth herein are expressly incorporated by reference.

Photoacoustic imaging techniques represent a powerful family of modalities capable of visualizing optical absorption contrast within optically scattering media. Commonly, short optical pulses in the nanosecond or picosecond range are fired into the sample where they are preferentially absorbed by specific species. This absorption of optical energy in turn creates local heat which generates a local pressure rise known as the initial pressure. Conventional photoacoustic techniques will then record the propagated ultrasound produced from these initial pressures some distance away from the original source, usually at the outer surface of the sample.

Photoacoustic modalities come in a variety of embodiments but can be classified into three larger families: photoacoustic tomography (PAT), acoustic-resolution photoacoustic microscopy (AR-PAM), and optical-resolution photoacoustic microscopy (OR-PAM). PAT devices tend to be structurally similar to conventional ultrasound imaging systems, consisting of an array of acoustic transducers with the addition of an optical delivery mechanism such as a light guide to direct excitation light into the sample. Following an excitation event, multiple acoustic signals are recorded along the acoustic array, and are later processed to reconstruct the original distribution of the acoustic sources which indicate the localized optical absorption. PATs tend to provide excellent penetration depth (>5 cm) but limited resolution (~500 um). AR-PAM devices tend to consist of a single focused acoustic transducer and an unfocused excitation beam. Images are acquired point-by-point by moving the focus of the transducer throughout the sample with multiple excitation capture events required for a single image. AR-PAMs tend to provide reduced penetration depth over PATs with further improved resolution characteristics bound by the acoustic diffraction limit. OR-PAMs utilize a focused excitation, and commonly also a focused transducer, to provide yet tighter resolution characteristics (<30 um) at the sacrifice of penetration depth (~1 mm, bound by optical diffusion).

Photoacoustic modalities have been demonstrably effective at imaging a wide variety of endogenous in vivo targets. These include but are not limited to, vascular structures from macro vessels to micro vessels, cellular structure taking advantage of ultraviolet absorption of DNA, visualization of lipid rich plaques, functional imaging including visualization of blood oxygen saturation distribution, and visualization of oxygen metabolism to name a few. As well, photoacoustic modalities are capable of imaging a wide variety of contrast agents which can be preferentially labeled to desired targets which otherwise to not provide endogenous contrast. However, since conventional photoacoustic techniques require physical coupling to the sample they are inappropriate for a wide variety of clinical applications such as burn diagnosis, interoperative imaging, monitoring of wound healing, and many endoscopic procedures.

Previous attempts at producing non-contact photoacoustic modalities have failed to provide affective in vivo visualization capabilities and have only demonstrated structural recovery within idealized phantoms. All of these efforts aimed to detect photoacoustic acoustic waves at some outer surface of the sample through some variety of interferometric technique. One example was proposed in (Gurton et al., US Patent Publication No. 2014/0185055) provided 30 µm lateral resolution. Another system entitled "Biological Tissue Inspection Method and System" is described in (Rousseau et al., US Patent Publication No. 2012/0200845).

More recently, an effective in vivo non-contact photoacoustic modality was reported known as photoacoustic remote sensing (PARS) microscopy (Haji Reza et al., US Patent Publication No. 2016/0113507, and Haji Reza et al., US Patent Publication No. 2017/0215738). The technology solved many of the sensitivity issues faced by previous efforts. Rather than inferring acoustic signals through surface oscillations, PARS monitors the back-reflected intensity of a secondary probe beam which is co-focused to the excitation spot. Large photoacoustic initial pressures in turn create non-trivial perturbations to the optical properties within the excited region through the elasto-optic effect. This sensing method is devoid of interference effects and thus provides great benefits in that is more tolerant to small perturbations within the system and within the sample, and collects a greater percentage of the photons returning from the sample improving sensitivity. PARS has demonstrated functional imaging capabilities in vivo, and is characterized by diffraction-limited optical resolution. PARS microscopy requires the use of two separate optical sources, commonly necessitating the use of multiple wavelengths. This can cause issues due to chromatic aberration within any refractive optic used, and within the sample itself. These aberrations can make co-alignment of the multiple foci challenging, and in some cases impossible to maintain over wide optical scans.

Embodiments of the present disclosure relate to a PARS microscope which is devoid or substantially devoid of unwanted chromatic effects. Such an architecture may provide benefits in terms of reducing optical exposure by ensuring ideal co-focus between the excitation and detection, and by using a pulsed detection which may limit temporal exposure. SS-PARS may be more cost effective to manufacture when compared with PARS as it does not require a secondary detection source. As well, by using a pulsed detection, SS-PARS may provide further imaging speed improvements over PARS, where continuous wave detection is used by shortening the interrogation time. In some embodiments, SS-PARS utilizes a single (i.e., only one or exactly one) optical source for both the excitation and the detection process. However, for reasons that will be discussed in later sections, a great number of technical challenges arise with this implementation, which are addressed in this disclosure.

SUMMARY

According to an aspect, there is provided a photoacoustic remote sensing system (PARS) for imaging subsurface structure in a sample known as single source photoacoustic remote sensing (SS-PARS) microscopy, which provides non-contact optical absorption contrast using a single (e.g., exactly one or only one) optical source pathway. This may be accomplished through the use of a pulsed optical source, which is split into two or more pulses, which are delayed and attenuated relative to each other allowing for the same source to both excite the sample and detect the generated PARS signals. This provides several benefits in terms of system cost, elimination or reduction of chromatic effects, along with a reduced sample optical exposure and improved signal fidelity over conventional PARS as it may take advantage of a pulsed detection. This may comprise a pulsed excitation beam configured to generate ultrasonic signals in the sample-path at an excitation location, a portion of the excitation beam returning from the sample that is indicative of the generated ultrasonic signals; an optical splitter to split the excitation path; an optical delay line to delay and attenuate one pulse relative to the other; and a processing unit for interpreting collected results. The excitation beam and an interrogation beam may be focused below the surface of the sample. The depth at which the beams are focused is not particularly limited, and may be, for example, 50 nm to 8 mm below the surface of the sample.

According to another aspect, there is provided an endoscopic SS-PARS which may provide significantly improved characteristics over an endoscopic PARS in terms of sensitivity and accuracy. Endoscopic SS-PARS may comprise a pulsed excitation beam configured to generate ultrasonic signals in the sample-path at an excitation location, a portion of the excitation beam returning from the sample that is indicative of the generated ultrasonic signals; an optical splitter to split the excitation path; an optical delay line to delay and attenuate one pulse relative to the other; an optical fiber cable having an input end and a detection end; and a processing unit for interpreting collected results.

For other embodiments of SS-PARS, the excitation source may comprise of a single or multiple sources which are pulsed, or CW and modulated. Excitation sources may be narrow-band and may cover a wide range of wavelengths or broadband individually providing wider spectra. This variety of excitation spectral content provides a means of/mechanism for implementing absorption-contrast spectral unmixing of the various target species in a sample. The optical beam splitters and combiners may comprise of an optical coupler such as a beam-splitting cube or polarizing beam-splitting cube for bulk optical implementation or a fiber coupler for fiber-based implementation. Multiple SS-PARS can be combined to provide desired wavelength contrast for multiplex and functional imaging of things such as blood oxygenation in vivo. A modality which uses multiple SS-PARS may be accomplished by combining more than one SS-PARS detection pathways to the same, or multiple imaging heads. The use of multiple SS-PARS detection pathways can provide access to a combination of different beam characteristics such as wavelength, pulse width, or pulse repetition rate to name a few.

Scanning of the interrogation location may be performed through optical scanning, such as with a galvo-mirror, MEMS mirror, resonant scanner, polygon scanner, etc., or through mechanical scanning of either the optics or the sample using single- or multiple-axes linear, or rotational stages. Axial scanning of the focus may be provided through variable-focal-length lenses (including voice-coil-driven, MEMS -based, piezoelectric-based, and tunable-acoustic-gradient lenses). Adaptive optics may be used to correct for aberrations in given applications such as ophthalmic imaging. Extraction of relevant signal data may be performed in a solely programmatic implementation, to a relevant circuit-based processor, or through some combination of the two.

Optical fibers described may be multi-mode, single-mode, polarization-maintaining, spun-fiber, or double-clad, or any combination of these.

The SS-PARS is distinct from PARS in that it: (1) does not require a separate detection source, (2) is intentionally implemented with a single (e.g., exactly one, or only one) optical wavelength per detection path for a given excitation event, (3) may require either an optical delay path, or burst-pulse excitation source, and (4) intentionally shares much of the optical components used for both exciting the sample and detecting optical modulations from the sample.

According to an aspect, a method for interrogating the optical properties of a sample may include generating optical pulses, separating the optical pulses, delaying one pulse relative to the other, attenuating one pulse relative to the other, combining the pulses, directing light towards a sample at a given location, and collecting light from a sample at a given location.

According to an aspect, a method for interrogating the optical properties of a sample may include generating optical pulses, separating the optical pulses, delaying one pulse relative to the other, attenuating one pulse relative to the other, combining the pulses, using another optical imaging modality, combining optical pathways, directing light towards a sample at a given location, and collecting light from a sample at a given location.

According to an aspect, an optical detector may comprise a processor configured to collect multiple pulses, and extract differences between multiple pulses.

Other aspects will be apparent from the description and claims below. In other aspects, the aspects described herein may be combined together in any reasonable combination as will be recognized by those skilled in the art.

BRIEF DESCRIPTION OF THE DRAWINGS

These and other features will become more apparent from the following description in which reference is made to the appended drawings, the drawings are for the purpose of illustration only and are not intended to be in any way limiting, wherein: In this patent document, the word "comprising" is used in its non-limiting sense to mean that items following the word are included, but items not specifically mentioned are not excluded. A reference to an element by the indefinite article "a" does not require that there be one and only one of the elements.

The scope of the following claims should not be limited by the preferred embodiments set forth in the examples above and in the drawings, but should be given the broadest interpretation consistent with the description as a whole.

Depiction of polarization optics orientation in figures does not necessarily represent true orientation. The difference should be obvious to anyone skilled in the art.

Figure 1:
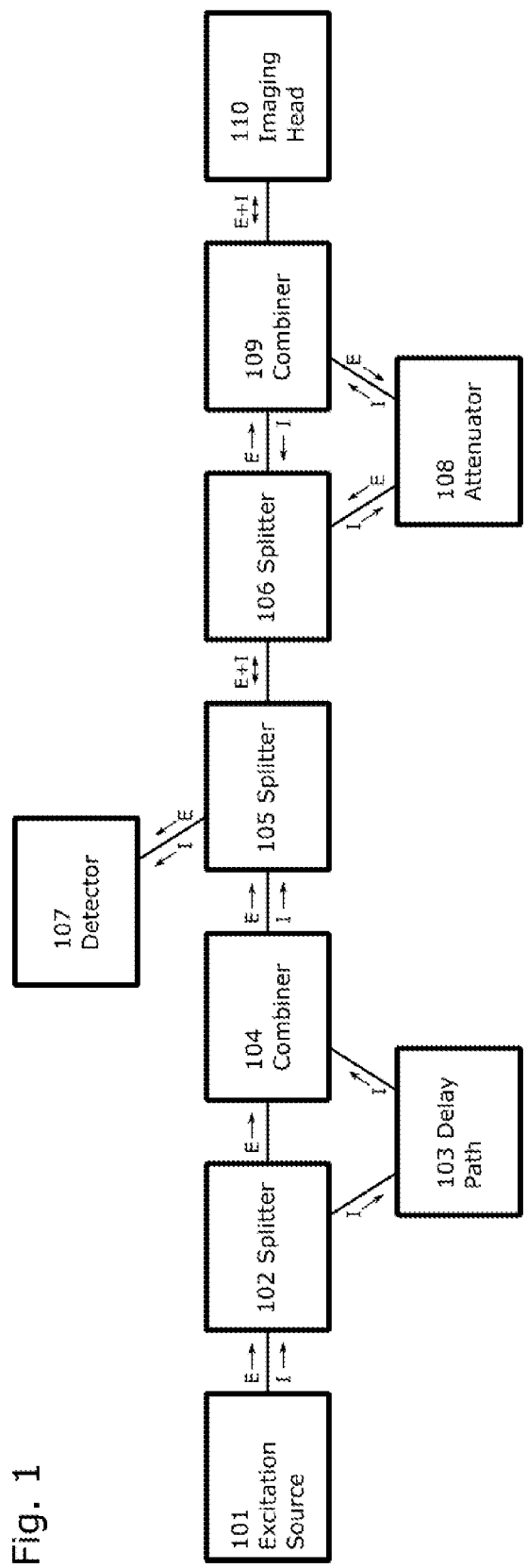

FIG. 1 depicts a schematic overview of a SS-PARS.

Figure 2:
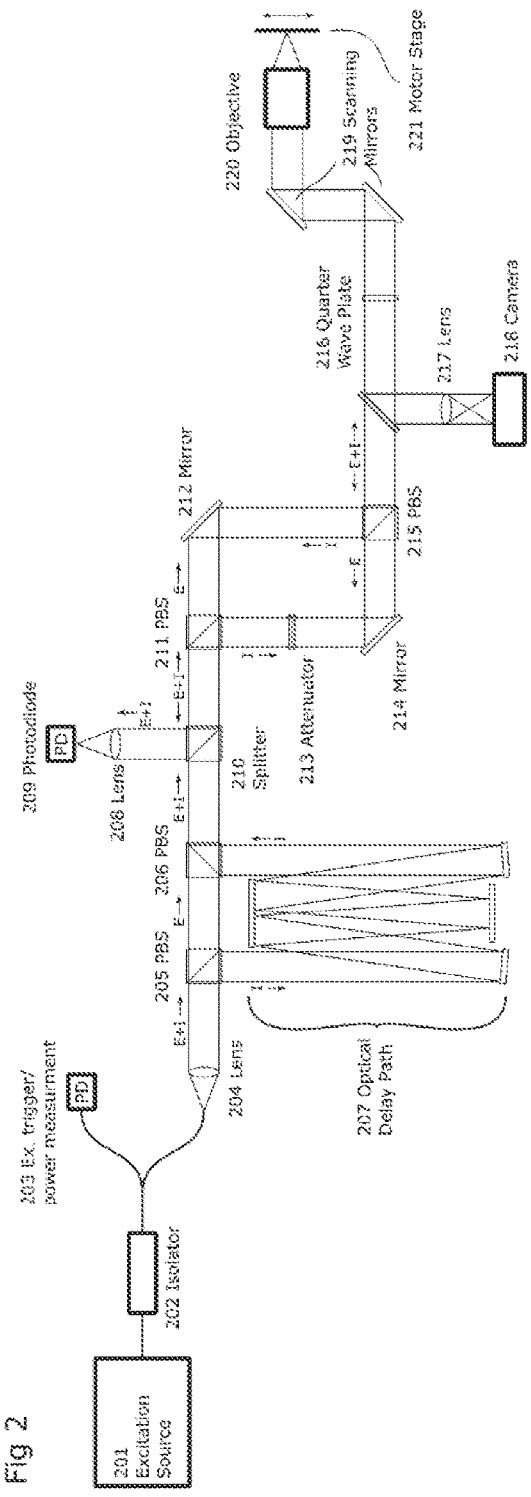

FIG. 2 depicts a schematic view of an example system layout for a free-space SS-PARS.

Figure 3:
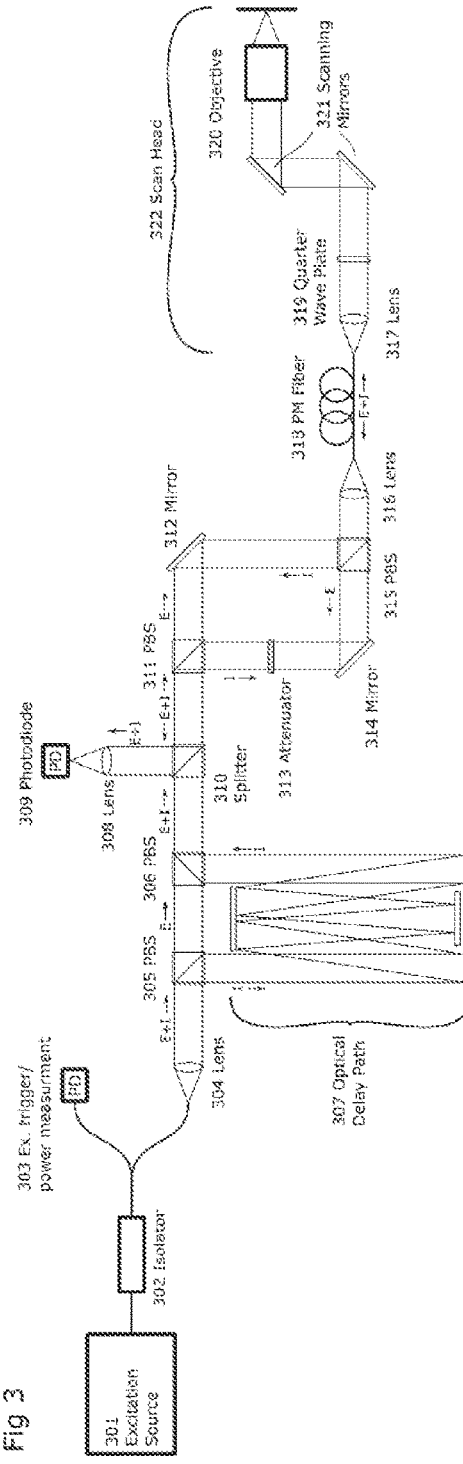

FIG. 3 depicts a schematic view of another example system layout for a free-space SS-PARS.

Figures 4, 5:
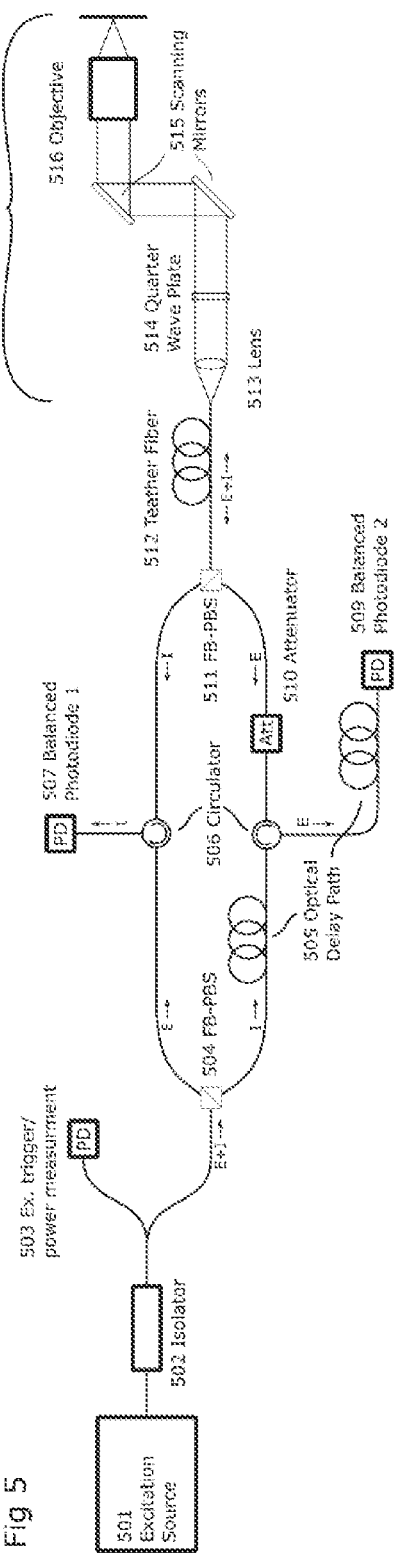

FIG. 4 depicts a schematic view of yet another example system layout for a free-space SS-PARS.

FIG. 5 depicts a schematic view of an example system layout for a fiber-based SS-PARS.

FIG. 6 depicts a schematic view of another example system layout for a fiber-based SS-PARS.

FIG. 7 depicts a schematic view of yet another example system layout for a fiber-based SS-PARS.

FIG. 8a is a graphical illustration of SS-PARS signals as they pass through an example system where the excitation pulse leads the interrogation pulse.

Figure 9:
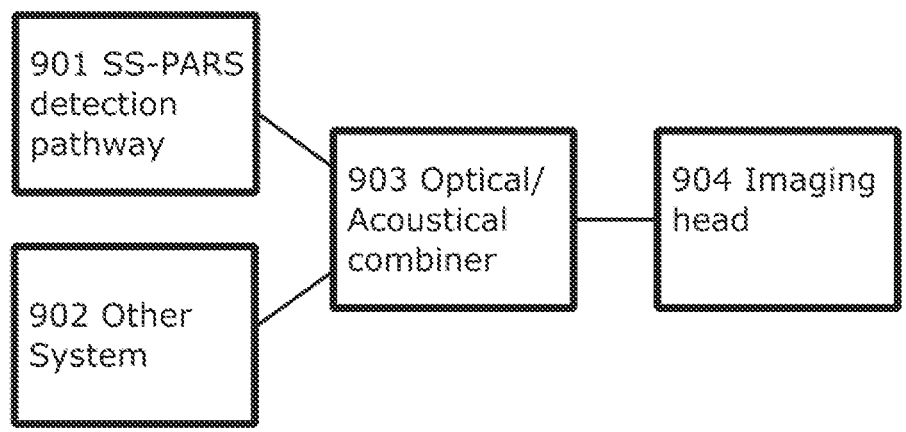

FIG. 8b is a graphical illustration of SS-PARS signals as they pass through an example system where the interrogation pulse leads the excitation pulse FIG. 9 depicts a schematic view of an example system layout where a SS-PARS is combined with another optical imaging modality.

Figure 10:
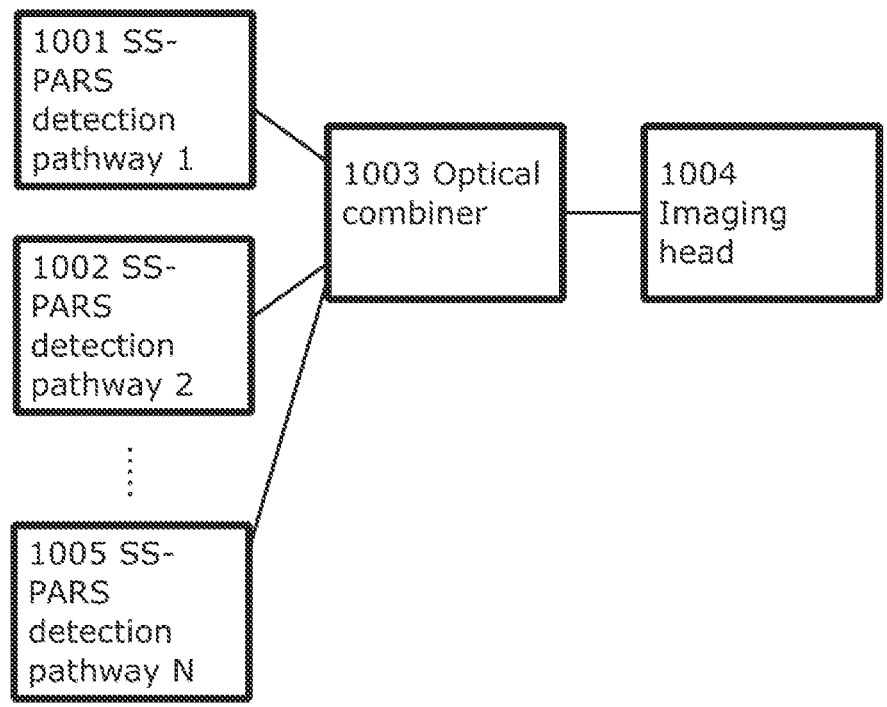

FIG. 10 depicts a schematic view of an example system layout where multiple SS-PARS detection pathways are combined.

FIG. 11 depicts a schematic view of an example system layout for a free-space SS-PARS which is polarization insensitive.

FIG. 12 depicts a schematic view of an example system layout for a fiber-based SS-PARS which is polarization insensitive.

Figure 13:
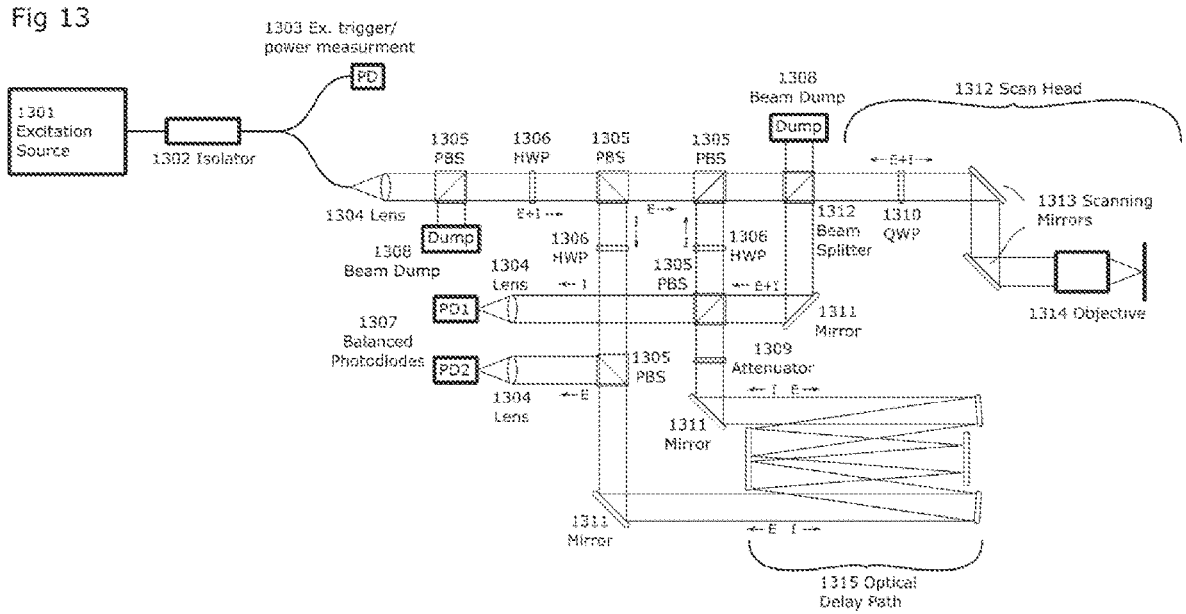

FIG. 13 depicts a schematic view of an example system layout for a free-space SS-PARS which uses balanced detection where the excitation pulse leads the interrogation pulse.

Figure 14:
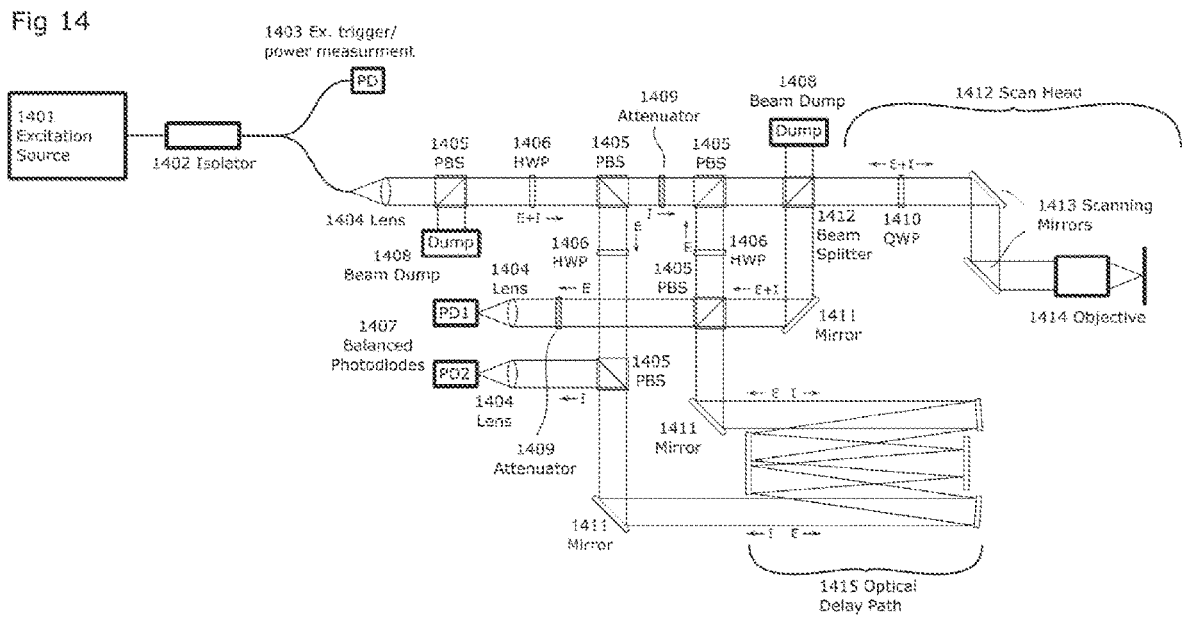

FIG. 14 depicts a schematic view of an example system layout for a free-space SS-PARS which uses balanced detection where the interrogation pulse leads the excitation pulse.

DETAILED DESCRIPTION

FIG. 1 shows a high-level overview of the SS-PARS pathways. A single pulse is created at the source (101) which is split (102). The interrogation component (I) is passed through a delay line (103) and recombined (104) with the excitation component (E). The signals may then be split again (106) allowing for attenuation (108) of the interrogation component to reduce surface radiation on the sample. The two pulses are then recombined again (109) and passed to the imaging head where they will interact with the sample. The excitation component will hit first producing pressure modulations in the sample which will then create PARS modulations in the interrogation component which follows it in time. These two components then return for detection. One way in which this may be carried out is depicted in FIG. 1, in which the components are again split (109). However, now the excitation component is passed through the attenuator (108) such that its intensity is reduced by the same amount as the interrogation component. The signals are then recombined (107) and directed (105) onto the detection photodiode (107) where they are detected. In this example, the generated electrical signals of the photodiode may require additional computational or analog processing to extract the desired PARS signals.

FIG. 1 shows a high-level overview of the SS-PARS pathways. A single pulse is created at the source (101) and may pass through an optical system including one or more splitters (102), (105), (106), one or more combiners (104), (109), one or more attenuators (108), a delay line or optical delay line (103), a detector (107), and/or an imaging head (110). For example, the single pulse may be which is split via a first splitter (102). The interrogation component (I) is passed through a delay line (103) and recombined via a first combiner (104) with the excitation component (E). The signals may then be split again via a second splitter (106) allowing for attenuation via an attenuator_(108) of the interrogation component to reduce surface radiation on the sample. The two pulses are then recombined again via a second combiner (109) and passed to the imaging head (110) where they will interact with the sample. The excitation component (E) will hit first producing pressure modulations in the sample which will then create PARS modulations in the interrogation component (I) which follows it in time. These two components then return for detection. One way in which this may be carried out is depicted in FIG. 1, in which the components are again split via a third splitter (109). However, now the excitation component (E) is passed through the attenuator (108) such that its intensity is reduced by the same amount as the interrogation component (I). The signals are then recombined via the second combiner (107109) and directed via the second splitter (105) onto the detection photodiode (107) where they are detected. In this example, the generated electrical signals of the photodiode (107) may require additional computational or analog processing to extract the desired PARS signals.

FIG. 2 highlights one possible implementation of SS-PARS. A polarized excitation source (201), which may consist of a pulsed fiber laser, may be coupled to an optical system including one or more lenses, mirrors, waveplates (e.g., quarter wave plate), collimators, beam combiners, attenuators, beam splitters, polarizing beam splitters, isolators, focusing assemblies, etc. that may direct, focus, and/or split the pulsed fiber laser. For example, the polarized excitation source (201) is coupled into free-space using a collimator such as a lens (204) with its polarization axis oriented such that the beam is split at a polarizing beam-splitter (205) which splits the beam into its polarization components. One component, named the interrogation component (I), is directed into an optical delay path (207), which may simply be a long optical path, such that it is delayed relative to the excitation component (E) when the two paths are recombined at another polarizing beam-splitter (206). After passing a non-polarizing beam-splitter (210) which may be used later on the returning light, the two components are again split at another polarizing beam-splitter (211) and the interrogation component is attenuated in an optical attenuator (213) to minimize optical exposure to the sample. The two components are recombined in yet another polarizing beam-splitter (215) and passed through a quarter wave plate (216) to circularize their polarizations. The components are then focused on to the sample using some form of objective lens or focusing assembly (220). In this implementation the interrogation spot can then be scanned about the sample using an optical scanning system such as a set of galvanometer mirrors (219) and/or a mechanical motor stage (221). The back-reflected components from the sample which are collected by the objective (220) will be significantly attenuated as compared to their magnitude before interacting with the sample, with the second interrogation component also having been modulated by the PARS mechanism, being indicative of the optical absorption of the interrogation spot. The two components pass back through the quarter waveplate (216) again where their polarization axes have now been flipped such that upon again interacting with the polarizing beam splitter (215) they are directed along the other path from which they arrived on. This may ensure that the excitation component now passes through the attenuator (213) such that, barring any PARS modulation to the interrogation component, the two pulses may be almost identical in intensity. The two components are recombined in a polarizing beam-splitter (211) and directed using a non-polarizing beam-splitter (210) on to a photodiode (209) for detection.

FIG. 4 highlights yet another possible implementation of SS-PARS. Here the tetherable scan head is replaced by an endoscope (422). Such a device may be used as a micro-endoscopy probe with an extremely small footprint (<1 mm), or as a full-size endoscopy probe. To maintain a compact profile, the optical scanning mirrors (421) could be implemented as MEMS devices placed after the focusing objective (420). Features in FIG. 4 having the same name, and similar numbering, as features from FIGS. 2 and 3, may be substantially identical to one another (e.g., excitation sources 201 and 401, isolators 202 and 402, etc.).

FIG. 5 highlights yet another possible implementation of SS-PARS. Here most of the free-space optics have been replaced by fiber-based components. The initial signal from the polarized excitation source (501) is split evenly by a fiber-based polarizing beam-splitter (504). The optical delay path (505) here may be simply implemented as the length of optical fiber. The interrogation component passes through the delay path (505) and is attenuated by a fiber-based attenuator (510) before being recombined in another fiber-based polarizing beam-splitter (511) acting as a polarizing coupler with the excitation component. The components may then be coupled into free-space beams using a collimator such as a lens (513), before being converted into circular polarization states by a quarter waveplate (514) as in FIGS. 2-4. In this particular example a tetherable scan head is used as previously described for FIG. 3 (322). The back-reflected components from the sample are converted back into linear polarization states again using the quarter waveplate (514). The two components are then split using the fiber-based polarizing beam-splitter (511) again. The interrogation component is now directed to the top path where a fiber-based circulator (506) directs it to one port of a balanced photodiode (507). The excitation component is directed through the attenuator (510) and then directed using another fiber-based circulator (506) into a similar optical delay path (505) to the first such that its total delay may match that of the interrogation component. The excitation component is then fed into another port of the balance photodiode (509). The balanced detection offered by this architecture may inherently provide analog extraction of the PARS-modulated signal. Features in FIG. 5 having the same name, and similar numbering, as features from FIGS. 2-4, may be substantially identical to one another (e.g., excitation sources 201 and 501, isolators 202 and 502, etc.).

FIG. 6 highlights yet another possible implementation of SS-PARS. This features the same SS-PARS processing architecture from a device described in FIG. 5, but with an endoscopic imaging head (617) like that described in FIG. 4 (422). Features in FIG. 6 having the same name, and similar numbering, as features from FIGS. 2-5, may be substantially identical to one another (e.g., excitation sources 201 and 601, isolators 202 and 602, etc.).

FIG. 7 highlights yet another possible implementation of SS-PARS. There are several small changes relative to the device described in FIG. 5. Here, the interrogation component is attenuated (705) before the optical delay path (706) such that undesired nonlinear effects (such as stimulated Rahman scattering) may be mitigated. This change requires that an additional fiber-based attenuator (710) must be added to the excitation component pathway before its optical delay path (711) which also may help to mitigate these undesired effects. Features in FIG. 7 having the same name, and similar numbering, as features from FIGS. 2-6, may be substantially identical to one another (e.g., excitation sources 201 and 701, isolators 202 and 702, etc.).

FIG. 8a shows an example of the intensity and excitation components as they progress through the SS-PARS. In this example, the interrogation pulse follows the excitation pulse to allow for the detection of PARS modulation on the interrogation pulse. Section 802 shows the initial pulse from the radiation source. Section 804 shows that the initial pulse has been split in two smaller components each with half the energy in this diagram. Section 806 shows the two components after the interrogation component has been delayed within the optical delay path and recombined with the excitation component. Section 808 shows that the interrogation component has been attenuated relative to the excitation component to reduce surface radiation exposure. Section 810 shows the two components after interacting with the sample. Both components have been attenuated from the reflection, however the interrogation component will additionally be modulated by the PARS effect created by the excitation component. Section 812 shows the excitation component having been attenuated such that, barring PARS modulation of the interrogation component, the two components would be at roughly equal energy. Section 814 shows the excitation component and the interrogation component recombined. For much of the described architectures, these two components may be detected at a single photodiode where the signal is processed by an analog or digital processor to extract the PARS modulation. However, if a balanced photodiode is used, such as in the architecture described in FIGS. 7 and 13, the excitation component may be delayed such that it matches that provided to the interrogation component. This may allow for balanced optical detection which will inherently extract the PARS signal.

FIG. 8b shows another example of the intensity and excitation components as they progress through the SS-PARS. In this example, the interrogation pulse leads the excitation pulse to allow for the detection of PARS modulation on the excitation pulse. Section 816 shows the initial pulse from the radiation source. Section 818 shows that the initial pulse has been split in two smaller components each with half the energy in this diagram. Section 820 shows the two components after the excitation component has been delayed within the optical delay path and recombined with the interrogation component. Section 822 shows that the interrogation component has been attenuated relative to the excitation component to reduce surface radiation exposure. Section 824 shows the two components after interacting with the sample. Both components have been attenuated from the reflection, however the excitation component will additionally be modulated by the PARS effect created by the excitation component. Section 826 shows the excitation component having been attenuated such that, barring PARS modulation of the excitation component, the two components would be at roughly equal energy. Section 828 shows the excitation component and the interrogation component recombined. For much of the described architectures these two components may be detected at a single photodiode where the signal is processed by an analog or digital processor to extract the PARS modulation. However, if a balanced photodiode is used such as in the architecture described in FIG. 14, the interrogation component may be delayed such that it matches that provided to the excitation component. This may allow for balanced optical detection which will inherently extract the PARS signal.

Other pulse schemes may be implemented featuring a variety of interrogation and excitation pulses which may be grouped or interlaced with each other. Furthermore, additional sources or SS-PARS may be added to further extend contrast capabilities. For example, between two SS-PARS interrogations, a mid-infrared source may be used to excite specific protein absorption peaks providing mid-infrared contrast, with resolution more akin to that provided by the SS-PARS wavelength. In another example, two SS-PARS may be combined to provide multiplex/functional imaging of multiple chromophores, such as 250 nm for DNA contrast, and 532 nm for hemoglobin contrast.

FIG. 9 shows an example of a SS-PARS detection pathway (901) combined using an optical beam combiner (903) with another optical modality (902) such as but not limited to bright-field microscopy, florescence microscopy, confocal microscopy, optical coherence tomography, optical coherence microscopy, Raman spectroscopy, coherent anti-Stokes Raman spectroscopy, multi photon microscopy, photoacoustic tomography, acoustic-resolution photoacoustic microscopy, optical-resolution photoacoustic microscopy, ultrasound, holography, quadrature microscopy, etc. These modalities may share the same imaging head (904) such that they can co-align captured information.

FIG. 10 shows an example of multiple SS-PARS detection pathways (1001, 1002, 1005) combined using an optical beam combiner (1003) such that they use the same imaging head (1004). This may allow for functional and multiplex imaging taking advantage of chromatic or intensity saturation contrast between species to determine relative concentrations.

FIG. 11 highlights yet another possible implementation of SS-PARS. Here the architecture is made to be polarization insensitive by removing polarization sensitive elements. This may compensate for polarization-dependent behavior in the sample. The splitter (1105) and combiner (1106) used to create two delayed pulses may be implemented as polarizing, or non-polarizing beam-splitters. Then both components are kept along the same path passing through a non-polarizing beam-splitter (1110) which will be used later on the return path, and coupled into a fiber-based scan head (1117) similar to that used in FIGS. 3, 7 (322, 718). The back-reflected components from the sample is then directed using the beam splitter (1110) onto a photodiode (1109) for detection. Features in FIG. 11 having the same name, and similar numbering, as features from FIGS. 2-7, may be substantially identical to one another (e.g., excitation sources 201 and 1101, isolators 202 and 1102, etc.).

FIG. 12 highlights yet another possible implementation of SS-PARS. Here the architecture is also polarization insensitive and features fiber-based components. The two components may be split in a fiber-based non-polarizing beam splitter (1204) where the interrogation component (I) is delayed using an optical delay path such as a length of fiber (1205). The two beams are then recombined using a fiber-based coupler (1213), and pass across a fiber-based circulator (1214) into the imaging scan head similar to FIGS. 3,7,11 (322, 718, 1117). The back-reflected components are then directed onto a photodiode (1206) for detection using the fiber-based circulator (1214). Features in FIG. 12 having the same name, and similar numbering, as features from FIGS. 2-7 and 11, may be substantially identical to one another (e.g., excitation sources 201 and 1201, isolators 202 and 1202, etc.).

FIG. 13 highlights yet another possible implementation of SS-PARS. Here the architecture may allow for free-space balanced detection of pulses. The addition of two waveplates (1306), two polarizing beamsplitters (1305), and a fold mirror (1311) between the main excitation path and delay path (1315) may facilitate providing a total time delay and total attenuation which is similar between both the excitation (E) and interrogation (I) pulses. As a result, both pulses can each be measured on separate ports of a balanced detector (1307) for analogue extraction of the PARS modulations. Features in FIG. 13 having the same name, and similar numbering, as features from FIGS. 2-7, 11, and 12 may be substantially identical to one another (e.g., excitation sources 201 and 1301, isolators 202 and 1302, etc.).

FIG. 14 highlights yet another possible implementation of SS-PARS. Here the architecture may allow for free-space balanced detection of pulses, like the exemplary implementation shown in FIG. 13. However, this implementation places the interrogation pulse before the excitation pulse. This may be necessary if, for a given target, the excitation pulse picks up PARS modulations. In this case, the interrogation must be made before excitation to capture the unperturbed sample. The primary difference between the exemplary system of FIG. 14 and the system of FIG. 13 is the different locations of attenuators (1409). Features in FIG. 14 having the same name, and similar numbering, as features from FIGS. 2-7, 11, 12, and 13 may be substantially identical to one another (e.g., excitation sources 201 and 1401, isolators 202 and 1402, etc.).

It will be apparent that other examples may be designed with different components to achieve similar results. Other alternatives may include various combinations of optical sources in terms of wavelength, pulse-width, pulse energy, and coherence length. Rather than a pulsed source, a continuous-wave source may be appropriately modulated. Various optical detectors (interferometric or non-interferometric) may be used such as photodiodes, avalanche photodiodes, balanced photodiodes, phototubes, photomultipliers, CMOS sensors/cameras, CCD sensors/cameras (including EM-CCD, intensified-CCDs, back-thinned and cooled CCDs), etc. The detected signal may be amplified by an RF amplifier, lock-in amplifier, trans-impedance amplifier, or other amplifier configuration. SS-PARS may use optical amplifiers to amplify detected light.

During in vivo imaging experiments, no agent or ultrasound coupling medium are required. However, the target can be prepared with water or any liquid such as oil before non-contact imaging session. No special holder or immobilization is required to hold the target during imaging sessions. An optical window may be placed between the sample and imaging head to facilitate flattening of the sample surface, or to facilitate differences in atmosphere between the sample and system.

Other advantages that are inherent to the structure will be apparent to those skilled in the art. The embodiments described herein are illustrative and not intended to limit the scope of the claims, which are to be interpreted in light of the specification as a whole.

The excitation beam may be any pulsed or modulated source of electromagnetic radiation including lasers or other optical sources. In one example, a nanosecond-pulsed laser was used. The excitation beam may be set to any wavelength suitable for taking advantage of optical (or other electromagnetic) absorption of the sample. The source may be monochromatic or polychromatic.

Multiple SS-PARS pathways can be combined using dichroic mirrors, prisms, beam splitters, polarizing beam splitters etc. They can also be focused using different optical paths.

A table top, handheld, endoscopic, surgical microscope, or ophthalmic SS-PARS system may be constructed based on principles known in the art. SS-PARS may be used for A-, B- or C- scan images for in vivo, ex vivo or phantom studies.

SS-PARS may be optimized in order to take advantage of a multi-focus design for improving the depth-of-focus of 2D and 3D OR-CG-PARS imaging. The chromatic aberration in the collimating and objective lens pair may be harnessed to refocus light from a fiber into the object so that each wavelength is focused at a slightly different depth location. Using these wavelengths simultaneously may be used to improve the depth of field and signal to noise ratio (SNR) of SS-PARS images. During SS-PARS imaging, depth scanning by wavelength tuning may be performed.

The SS-PARS system may be combined with other imaging modalities such as fluorescence microscopy, two-photon and confocal fluorescence microscopy, Coherent-Anti-Raman-Stokes microscopy, Raman microscopy, Optical coherence tomography, other photoacoustic and ultrasound systems, etc. Combination is achievable through combining modalities before the primary focusing optics with beam splitters or dichroic mirrors to name a few methods. This could permit imaging of the microcirculation, blood oxygenation parameter imaging, and imaging of other molecularly-specific targets simultaneously, a potentially important task that is difficult to implement with only fluorescence-based microscopy methods. A multi-wavelength visible laser source may also be implemented to generate photoacoustic signals for functional or structural imaging.

Polarization analyzers may be used to decompose detected light into respective polarization states. The light detected in each polarization state may provide information about ultrasound-tissue interaction.

Topological tracking may be implemented to account for roughness in the sample surface allowing for improved imaging consistency with less user preparation.

APPLICATIONS

It will be understood that the system described herein may be used in various ways, such as those purposes described above, and also may be used in other ways to take advantage of the aspects described above. A non-exhaustive list of applications is discussed below.

The system may be used for imaging angiogenesis for different pre-clinical tumor models.

The system may be used to image: (1) histological samples; (2) cell nuclei; (3) proteins; (4) cytochromes; (5) DNA; (6) RNA; and (7) lipids. The system also may be used for replacing a catheterization procedure, gastroenterological applications, single-excitation pulse imaging over an entire field of view, imaging of tissue, imaging of cells, imaging of scattered light from object surfaces, imaging of absorption-induced changes of scattered light, or non-contact imaging of optical absorption.

The system may be used for imaging DNA absorption peaks to provide label-free visualization of cellular structure. This could be used intraoperatively, or on ex vivo samples with the goal of directing resection surgery and providing some early indication of margin status. The single wavelength implementation may improve flexibility of the imaging device such that the focus can be more easily scan throughout a complex sample without need for correcting of chromatic effects.

Another possible application of SS-PARS is with ophthalmic imaging. Again, since the system uses a single wavelength, chromatic effects introduced by the complex optics of the eye may be greatly reduced or negated entirely. This could have profound impact for a variety of ophthalmic applications such as detection and characterization of glaucoma, age-related macular degeneration, diabetic retinopathy and any related eye diseases.

Like conventional PARS, SS-PARS Can be used to provide multiplex- and functional imaging of a variety of endogenous species in vivo. One popular target would be oxygenated and deoxygenated hemoglobin whose relative concentration may be measured with SS-PARS. This allows for real time visualization of blood oxygenation and blood metabolism down to the capillary level which can provide invaluable information to clinicians and researchers alike. As well, remote/non-invasive intratumoural assessment of glucose concentration may be performed by detection of endogenous glucose absorption peeks. Other common endogenous targets include DNA, RNA, melanin, and lipids.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including anti-angiogenic drugs; (11) imaging response to radiotherapy.

The system may be useful in estimating oxygen saturation using multi-wavelength photoacoustic excitation and SS-PARS detection and applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using SS-PARS imaging to estimate oxygen saturation, and an auxiliary method to estimate blood flow in vessels flowing into and out of a region of tissue.

The system may also have some gastroenterological applications, such as imaging vascular beds and depth of invasion in Barrett's esophagus and colorectal cancers. Depth of invasion is key to prognosis and metabolic potential. Gastroenterological applications may be combined or piggy-backed off of a clinical endoscope and the miniaturized SS-PARS system may be designed either as a stand-alone endoscope or fit within the accessory channel of a clinical endoscope.

The system may have some surgical applications, such as functional imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

Other examples of applications may include SS-PARS imaging of contrast agents in clinical or pre-clinical applications; identification of sentinel lymph nodes; non- or minimally-invasive identification of tumors in lymph nodes; imaging of genetically-encoded reporters such as tyrosinase, chromoproteins, fluorescent proteins for pre-clinical or clinical molecular imaging applications; imaging actively or passively targeted optically absorbing nanoparticles for molecular imaging; and imaging of blood clots and potentially staging the age of the clots.

Possible applications of SS-PARS structural, multiplex, and functional imaging capabilities may include assessment of organoid growth, monitoring of developing embryos, assessment of biofilm composition and assessment of tooth decay to name a few. It is also important to note that the SS-PARS may be applicable outside of biological imaging. Some examples of this may be the assessment of non-living structures such as evaluating the composition of paintings to do non-invasive confirmation of authenticity, evaluation of archeological artefacts, manufacturing quality control and quality assurance to name a few.

In some embodiments, any suitable technology, such as, e.g., OCT, can be used for surface topology (for constant- or variable-depth focusing for photoacoustic remote sensing technologies) before imaging with SS-PARS.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A sensing system for imaging a sample, comprising:
exactly one laser source configured to generate:
an excitation beam configured to generate signals in the sample at an excitation location, and
wherein the exactly one laser source is also configured to generate an interrogation beam incident on the sample at the excitation location, a portion of the interrogation beam returning from the sample that is indicative of the generated signals, wherein the excitation beam or the interrogation beam are focused below a surface of the sample;
a detector configured to detect the returning portion of the interrogation beam; and
a processor configured to calculate an image of the sample based on the detected returning portion of the interrogation beam from below the surface of the sample.

2. The system of claim 1, further including:
a beam splitter configured to split an output of the exactly one laser source into the excitation beam and the interrogation beam; and
an optical delay line configured to delay and/or attenuate the interrogation beam relative to the excitation beam.

3. The system of claim 2, further including a beam combiner configured to combine the excitation beam and the delayed and/or attenuated interrogation beam.

4. The system of claim 2, wherein, between the beam splitter and the beam combiner, the delayed and/or attenuated interrogation beam travels along a longer optical path than the excitation beam.

5. The system of claim 2, wherein the beam splitter is a polarizing beam splitter.

6. The system of claim 2, further including:
a first wave plate and a second wave plate;
a second beam splitter and a third beam splitter, wherein the second beam splitter and the third beam splitter are polarizing beam splitters; and
a fold mirror,
wherein the first wave plate, the second wave plate, the second beam splitter, the third beam splitter, and the fold mirror are between a main excitation path and a path of the optical delay line.

7. The system of claim 1, further including a beam splitter configured to direct the interrogation beam to an optical attenuator to reduce surface radiation on the sample.

8. The system of claim 1, further including an optical attenuator and a beam combiner arranged such that, after the interrogation beam passes through the optical attenuator, the interrogation beam and the excitation beam are combined at the beam combiner.

9. The system of claim 8, wherein after passing through the beam combiner, the combined interrogation and excitation beam are configured to pass through a polarizer configured to control and/or modify their polarizations.

10. The system of claim 9, wherein, after passing through the wave plate, the combined interrogation beam and excitation beam are directed to the optical system.

11. The system of claim 1, further comprising a polarizer configured to control and/or modify a polarization of the interrogation beam, wherein only the polarization of the interrogation beam is controlled and/or modified, and wherein the processor is configured to identify a change in the polarization of the returning portion of the interrogation beam induced by the sample.

12. The system of claim 1, wherein the system is used in one or more of the following applications:
imaging histological samples;
imaging cell nuclei;
imaging proteins;
imaging DNA;
imaging RNA;
imaging lipids;
imaging of blood oxygen saturation;
imaging of tumor hypoxia;
imaging of wound healing, burn diagnostics, or surgery;
imaging of microcirculation;
blood oxygenation parameter imaging;
estimating blood flow in vessels flowing into and out of a region of tissue;
imaging of molecularly-specific targets;
imaging angiogenesis for pre-clinical tumor models;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;

imaging response to chemotherapeutics;
imaging response to anti-angiogenic drugs;
imaging response to radiotherapy;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots;
staging an age of blood clots;
remote or non-invasive intratumoural assessment of glucose concentration by detection of endogenous glucose absorption peeks;
assessment of organoid growth;
monitoring of developing embryos;
assessment of biofilm composition;
assessment of tooth decay;
assessment of non-living structures;
evaluating the composition of paintings for non-invasive confirmation of authenticity;
evaluation of archeological artifacts;
manufacturing quality control;
manufacturing quality assurance;
replacing a catheterization procedure;
gastroenterological applications;
single-excitation pulse imaging over an entire field of view;
imaging of tissue;
imaging of cells;
imaging of scattered light from object surfaces;
imaging of absorption-induced changes of scattered light; or non-contact imaging of optical absorption.

13. The system of claim 1, wherein the excitation beam and the interrogation beam are focused within 1 mm of the surface of the sample.

14. The system of claim 1, wherein at least one of the excitation beam or the interrogation beam is focused at a depth greater than 1 pm below the surface of the sample.

15. The system of claim 14, wherein:
the focusing assembly is configured to focus the excitation beam at a first focal point and the interrogation beam at a second focal point, the first and second focal points being below the surface of the sample; and
at least one of the first or second focal points are spaced below the surface of the sample at a depth that is greater than a focal zone of the respective at least one of the excitation beam and the interrogation beam.

16. The system of claim 14, wherein the focusing assembly is configured to focus the excitation beam at a first focal point and the interrogation beam at a second focal point, wherein the first and the second focal points are at a depth below the surface of the sample that is from 50 nm to 8 mm.

17. The system of claim 1, further comprising a focusing assembly configured to focus the excitation beam or the interrogation beam below the surface of the sample.

18. The system of claim 1, wherein the excitation beam has a focal point that is laterally within a focal zone of the interrogation beam; or the interrogation beam has a focal point that is laterally within a focal zone of the excitation beam.

19. A method of visualizing details in a sample, the method comprising the steps of:
generating signals in the sample at an excitation location using exactly one laser source configured to generate an excitation beam, the excitation beam being focused below a surface of the sample;
interrogating the sample using the exactly one laser source, wherein the exactly one laser source is configured to generate an interrogation beam directed toward the excitation location of the sample, the interrogation beam being focused below the surface of the sample;
detecting a portion of the interrogation beam returning from the sample; and
calculating an image based on the detected returned portion of the interrogation beam.

20. A method of visualizing details in a sample, the method comprising the steps of:
receiving, via a portion of a first beam returning from the sample, one or more signals, wherein the one or more signals were generated in the sample at an excitation location by a second beam using exactly one laser source, the second beam being directed toward the excitation location and focused below a surface of the sample, and wherein the first beam was generated using the exactly one laser source and was focused below the surface of the sample; and
determining an image based on the received one or more signals.

* * * * *

UNITED STATES PATENT AND TRADEMARK OFFICE
CERTIFICATE OF CORRECTION

| | |
|---|---|
| PATENT NO. | : 11,950,882 B2 |
| APPLICATION NO. | : 18/069791 |
| DATED | : April 9, 2024 |
| INVENTOR(S) | : Parsin Haji Reza et al. |

It is certified that error appears in the above-identified patent and that said Letters Patent is hereby corrected as shown below:

In the Specification

Column 1, Line 8, delete "Mar.13," and insert --Mar. 13,--.

In the Claims

Column 16, Line 6, in Claim 14, delete "pm" and insert --µm--.

Signed and Sealed this
Eleventh Day of June, 2024

*Katherine Kelly Vidal*

Katherine Kelly Vidal
*Director of the United States Patent and Trademark Office*